United States Patent
Church et al.

(10) Patent No.: US 10,494,662 B2
(45) Date of Patent: *Dec. 3, 2019

(54) METHOD FOR GENERATING A THREE-DIMENSIONAL NUCLEIC ACID CONTAINING MATRIX

(71) Applicant: President and Fellows of Harvard College, Cambridge, MA (US)

(72) Inventors: George M. Church, Brookline, MA (US); Je-Hyuk Lee, Allston, MA (US); Richard C. Terry, Carlisle, MA (US); Evan R. Daugharthy, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/786,921

(22) Filed: Oct. 18, 2017

(65) Prior Publication Data

US 2018/0051322 A1 Feb. 22, 2018

Related U.S. Application Data

(63) Continuation of application No. 14/774,282, which is a continuation of application No. PCT/US2014/018580, filed on Feb. 26, 2014, now Pat. No. 10,138,509.

(60) Provisional application No. 61/777,383, filed on Mar. 12, 2013.

(51) Int. Cl.
| | |
|---|---|
| *C12Q 1/68* | (2018.01) |
| *C12P 19/34* | (2006.01) |
| *C12Q 1/6806* | (2018.01) |
| *C12Q 1/6874* | (2018.01) |
| *C12Q 1/6844* | (2018.01) |
| *C12Q 1/6869* | (2018.01) |

(52) U.S. Cl.
CPC ............ *C12Q 1/6806* (2013.01); *C12P 19/34* (2013.01); *C12Q 1/6844* (2013.01); *C12Q 1/6869* (2013.01); *C12Q 1/6874* (2013.01)

(58) Field of Classification Search
CPC .......................... C12Q 1/6806; C12Q 1/6869
See application file for complete search history.

(56) References Cited

U.S. PATENT DOCUMENTS

| | | | |
|---|---|---|---|
| 4,123,610 A | 10/1978 | Summerton et al. | |
| 4,981,985 A | 1/1991 | Kaplan et al. | |
| 5,563,056 A | 10/1996 | Swan et al. | |
| 5,830,708 A | 11/1998 | Naughton | |
| 7,323,305 B2* | 1/2008 | Leamon | B01L 3/502707 435/175 |
| 7,473,767 B2 | 1/2009 | Dimitrov | |
| 8,551,710 B2 | 10/2013 | Bernitz et al. | |
| 9,217,151 B2 | 12/2015 | Yin et al. | |
| 2002/0015952 A1* | 2/2002 | Anderson | B01J 19/0046 435/6.11 |
| 2003/0148335 A1 | 8/2003 | Shen et al. | |
| 2004/0077014 A1 | 4/2004 | Becker | |
| 2004/0248144 A1 | 12/2004 | Mir | |
| 2004/0259190 A1 | 12/2004 | Naughton | |
| 2005/0106629 A1 | 5/2005 | McGrath et al. | |
| 2005/0147981 A1 | 7/2005 | Yamakawa et al. | |
| 2005/0233318 A1 | 10/2005 | Chee et al. | |
| 2006/0024711 A1 | 2/2006 | Lapidus et al. | |
| 2006/0177833 A1 | 8/2006 | Brenner | |
| 2006/0234261 A1 | 10/2006 | Pierce et al. | |
| 2006/0248349 A1 | 11/2006 | Rathjen et al. | |
| 2006/0292611 A1 | 12/2006 | Berka et al. | |
| 2007/0020650 A1 | 1/2007 | Kahvejian | |
| 2007/0087362 A1 | 4/2007 | Church et al. | |
| 2007/0117109 A1 | 5/2007 | Rothemund | |
| 2007/0117177 A1 | 5/2007 | Luo et al. | |
| 2008/0176769 A1 | 7/2008 | Rank et al. | |
| 2009/0005259 A1 | 1/2009 | Drmanac | |
| 2009/0208965 A1 | 8/2009 | Tafas et al. | |
| 2009/0246879 A1 | 10/2009 | Drmanac et al. | |
| 2010/0009868 A1 | 1/2010 | Yan et al. | |
| 2010/0047924 A1 | 2/2010 | Webster et al. | |
| 2010/0223276 A1 | 9/2010 | Al-Shameri et al. | |
| 2010/0268478 A1 | 10/2010 | Andregg et al. | |
| 2011/0020291 A1 | 1/2011 | Banerjee et al. | |
| 2011/0086774 A1 | 4/2011 | Dunaway | |
| 2011/0092376 A1 | 4/2011 | Colston, Jr. et al. | |
| 2011/0245111 A1 | 10/2011 | Chee | |
| 2011/0257031 A1 | 10/2011 | Bodeau et al. | |
| 2011/0294135 A1 | 12/2011 | Carlson | |
| 2012/0040397 A1* | 2/2012 | Luo | A61K 9/06 435/68.1 |
| 2012/0122712 A1 | 5/2012 | Goldstein | |
| 2013/0017229 A1 | 1/2013 | Mooney et al. | |
| 2013/0245096 A1 | 9/2013 | Abitbol | |
| 2014/0087378 A1 | 3/2014 | Chatre et al. | |
| 2014/0220587 A1 | 8/2014 | Green, Jr. et al. | |
| 2015/0133319 A1 | 5/2015 | Fu et al. | |

(Continued)

FOREIGN PATENT DOCUMENTS

| | | |
|---|---|---|
| KR | 20080003402 A | 1/2008 |
| WO | 9746704 A1 | 12/1997 |

(Continued)

OTHER PUBLICATIONS

Grompe (1993) Nature Genetics DOI: 10.1038/ng1093-111.*
Thisse et al. 2008 Nature protocols vol. 3 No. 1 pp. 59-69. Doi:10.1038/nprot.2007.514.*
International Search Report issued from corresponding PCT/US14/18580, dated Jul. 11, 2014.
Dec. 18, 2014 (PCT) International Preliminary Report—App PCT/US2013/044241.
Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

(Continued)

*Primary Examiner* — David C Thomas
(74) *Attorney, Agent, or Firm* — Banner & Witcoff, Ltd.

(57) ABSTRACT

Methods of making a three-dimensional matrix of nucleic acids within a cell is provided.

26 Claims, 10 Drawing Sheets

Specification includes a Sequence Listing.

(56) References Cited

U.S. PATENT DOCUMENTS

| | | |
|---|---|---|
| 2016/0024555 A1 | 1/2016 | Church et al. |
| 2016/0265046 A1 | 9/2016 | Zhang et al. |
| 2017/0212983 A1 | 7/2017 | Cai et al. |

FOREIGN PATENT DOCUMENTS

| | | |
|---|---|---|
| WO | 01/26708 A1 | 4/2001 |
| WO | 2007086900 A2 | 8/2007 |
| WO | 2007/121489 A2 | 10/2007 |
| WO | 2008069973 A2 | 6/2008 |
| WO | 2009046149 A1 | 4/2009 |
| WO | 2010080134 A1 | 7/2010 |
| WO | 2011/143583 A1 | 11/2011 |
| WO | 2012005595 A2 | 1/2012 |
| WO | 2012/058638 A2 | 5/2012 |
| WO | 2012150035 A1 | 11/2012 |
| WO | 2013/055995 A2 | 4/2013 |
| WO | 2014/0163886 A1 | 10/2014 |
| WO | 2014/182528 A2 | 11/2014 |
| WO | 2015/118029 A1 | 8/2015 |

OTHER PUBLICATIONS

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Eliscovich et al. mRNA on the move: The road to its biological destiny. Journal of Biological Chemistry, vol. 288, No. 28, pp. 20361-20368, Jul. 2013, in press May 2013 (Year: 2013).

Extended European Seach Report issued in corresponding European Application No. 12860433.7, dated Aug. 13, 2015.

Ginart, P et al. RNA Sequencing In Situ. Nat Biotechnol. Jun. 2014, vol. 32, No. 6; pp. 543-544; Doi: 10.1038/nbt.2921.

Han et al. "Quantum-dot-tagged microbeads for multiplexed optical coding of biomolecules". Nature Biotechnology, vol. 19, 99. 631-635 (Jul. 31, 2001).

International Search Report and Written Opinion issued in corresponding International Application No. PCT/US2012/071398, dated Apr. 8, 2013.

Jambhekar et al. Cis-acting determinants of asymmetric, cytoplasmic RNA transport. RNA, vol. 13, pp. 625-642, 2007 (Year: 2007).

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).

Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Matlin et al. Spatial expression of the genome: the signal hypothesis at forty. Nature Reviews. Molecular Cell Biology, vol. 12, No. 5, pp. 333-340, May 2011, Epub Apr. 2011. (Year 2011).

Meeks et al. Characterization of genes encoding poly(A) polymerases in plants: Evidence for duplication and functional specialization. PLoS One, vol. 4, No. 11, e8082, Nov. 2009, printed as pp. 1/10-10/10. (Year 2009).

Office Action issued for corresponding European Patent Application No. 12780609.9, dated Sep. 23, 2015.

Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year 2006).

Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.

Seo, et al. Four-color DNA sequencing by synthesis on a chip using photocleavable fluorescent nucleotides. Proceeding of the National Academy of Sciences, Apr. 2005, 102 (17) 5926-5931.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

Singer-Kruger et al. Here, there, everywhere. RNA Biology, vol. 11, No. 8, pp. 1031-1039, Aug. 2014. (Year: 2014).

Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year 2004).

Weis et al. Protein targeting to subcellular organelles via mRNA localization. Biochimica et Biophysica Acta, vol. 1833, pp. 260-273, 2013, available online Apr. 2012 (Year 2012).

Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.

International Search Report and Written Opinion based on PCT/US2018/027583 dated Jun. 29, 2018.

Soderberg, Ola et al.,"Direct observation of individual endogenous protein complexes in situ by proximity ligation," Nature Methods, Dec. 2006, pp. 995-1000, vol. 3, No. 12, Nature Publishing Group.

Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.

Cao, Yi et al.," In-situ immuno-PCR to detect antigens," The Lancet, Sep. 16, 2000, pp. 1002-1003, vol. 356.

Sano, Takeshi et al. "Immuno-PCR: Very Sensitive Antigen Detection by Means of Specific Antibody-DNA Conjugates," Science, Oct. 2, 1992, pp. 120-122, vol. 258.

Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].

Extended European Search Report dated May 13, 2019 for EP Application No. 16862929.3.

Lee, Je Hyuk et al., "Fluorescent in situ sequencing (FISSEQ) or RNA for gene expression profiling in intact cells and issues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.

Extended European Search Report dated May 21, 2019 for European Application No. 16862945.9.

\* cited by examiner

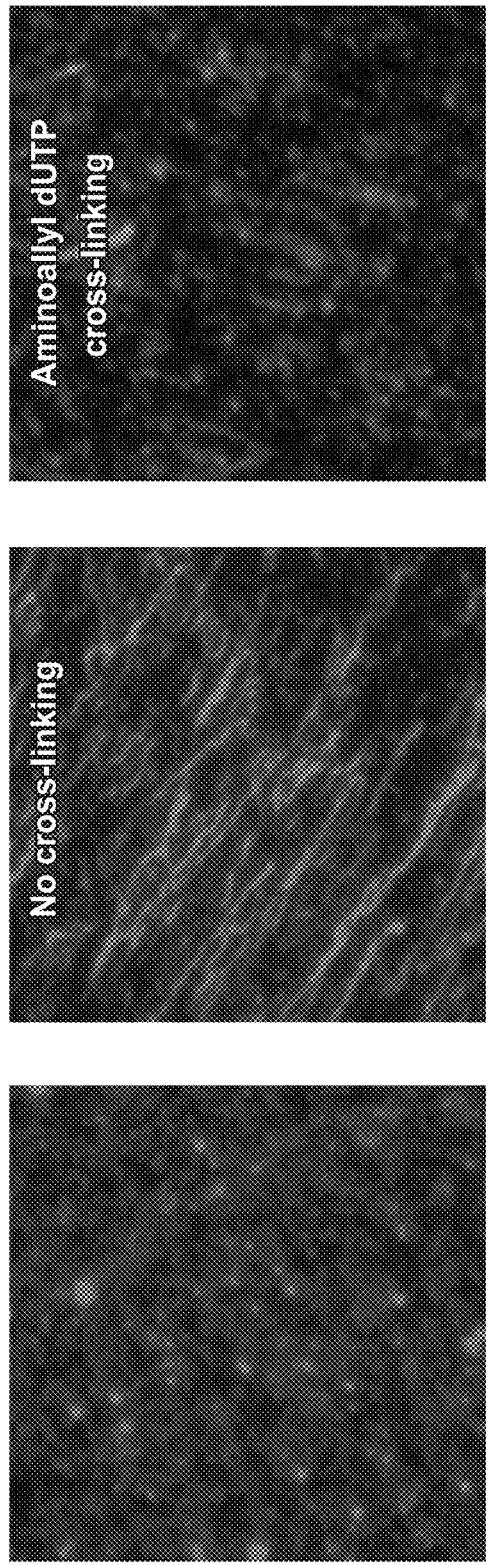
FIG. 7C  No shear stress
DNA amplicons (0.5–2 um diameter)
FIG. 7D  5 min high shear stress
No cross-linking
Stretched out DNA amplicons (20–100 um diameter)
FIG. 7E  5 min high shear stress
Aminoallyl dUTP cross-linking
Morphologically preserved DNA amplicons DNA amplicons crosslinked in fibroblasts

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: PCR primer

<400> SEQUENCE: 1
tctcgggaac gctgaaga                                                18

METHOD FOR GENERATING A THREE-DIMENSIONAL NUCLEIC ACID CONTAINING MATRIX

RELATED APPLICATION DATA

This application is a continuation application which claims priority to U.S. patent application Ser. No. 14/774,282, filed on Sep. 10, 2015, which is a National Stage Application under 35 U.S.C. 371 of co-pending PCT Application No. PCT/US2014/018580 designating the United States and filed Feb. 26, 2014; which claims the benefit of U.S. Provisional Application No. 61/777,383 and filed Mar. 12, 2013 each of which are hereby incorporated by reference in their entireties.

STATEMENT OF GOVERNMENT INTERESTS

This invention was made with Government support under grant number RC2HL102815 awarded by NHLBI and 1P50HG005550 awarded by NHGRI. The Government has certain rights in the invention.

FIELD OF THE INVENTION

The present invention relates to methods of making a three-dimensional matrix of nucleic acids and amplifying, detecting and sequencing such nucleic acids within the matrix.

BACKGROUND OF THE INVENTION

Since many gene products such as RNA and proteins are enriched in regions where they function, their location provides an important clue to their function. This property has been used for in situ fluorescent hybridization, immunohistochemistry and tissue-specific reporter assays in numerous areas of biological research.

Current methods involve extracting nucleic acid molecules from their native environment or making synthetic nucleic acid molecules, amplifying them in solution and placing them on a flat array surface or beads for gene detecting via hybridization or sequencing, making it impossible to identify the cellular origin of individual nucleic acids.

SUMMARY

Embodiments of the present invention are directed to methods of making a three dimensional matrix of nucleic acids. Embodiments of the present invention are directed to methods of making a three dimensional matrix including nucleic acids covalently bound into a matrix or into or to a matrix material. The nucleic acids may be co-polymerized with the matrix material or cross-linked to the matrix material or both. According to one aspect, a plurality of nucleic acid sequences of certain length, such as DNA or RNA sequences are part of a three-dimensional copolymer. The nucleic acids may then be amplified and sequenced in situ, i.e. within the matrix. The three-dimensional matrix of nucleic acids provides, in a certain aspect, an information storage medium where the nucleic acids, i.e. a sequence of one or more nucleotides, represent stored information which can be read within the three-dimensional matrix. According to one aspect, nucleic acids such as DNA or RNA sequences of given length are covalently attached to a matrix material to preserve their spatial orientation in the x, y and z axes within the matrix. It is to be understood that the three dimensional matrix may include a matrix material and that the term copolymer, matrix and matrix material may be used interchangeably.

According to one aspect, methods described herein are directed to immobilizing naturally occurring nucleic acids within their native environment, such as within a cell or within a tissue sample. The three dimensional nucleic acid matrix can be generated in situ in a cell or tissue sample to preserve the naturally occurring nucleic acid sequence diversity (such as DNA and RNA) and spatial orientation in cells, tissues or any other complex biomaterial. According to this aspect, the location of nucleic acids and their relative position is identified as a three dimensional structure, such as within subcellular compartments, within cells, within tissues, as three dimensional nucleic acid assemblies, as three dimensional nucleic acid material, etc. The nucleic acids can be amplified and sequenced, if desired, in situ thereby providing positional information of the nucleic acids within the cell or tissue.

According to a related aspect, nucleic acids of interest, whether naturally occurring or synthetic, can be present within a three dimensional matrix material and covalently attached to the three dimensional matrix material such that the relative position of each nucleic acid is fixed, i.e. immobilized, within the three dimensional matrix material. In this manner, a three-dimensional matrix of covalently bound nucleic acids of any desired sequence is provided. Each nucleic acid has its own three dimensional coordinates within the matrix material and each nucleic acid represents information. In this manner, a large amount of information can be stored in a three dimensional matrix. Individual information-encoding nucleic acids, such as DNA or RNA can be amplified and sequenced in situ, i.e., within the matrix, thereby enabling a large amount of information to be stored and read in a suitable three dimensional material.

According to a further aspect, the nucleic acids can be amplified to produce amplicons within the three dimensional matrix material. The amplicons can then be covalently attached to the matrix, for example, by copolymerization or cross-linking. This results in a structurally stable and chemically stable three dimensional matrix of nucleic acids. According to this aspect, the three dimensional matrix of nucleic acids allows for prolonged information storage and read-out cycles. The nucleic acid/amplicon matrix allows for high throughput sequencing of a wide ranging array of biological and non-biological samples in three dimensions.

According to certain aspects, a three dimensional nucleic acid matrix is provided where a plurality of nucleic acid molecules, such as DNA or RNA, amplicons or nucleic acid structural units are immobilized, such as by covalent bonding to the matrix, in a three dimensional space relative to one another. In this context, the nucleic acid molecules are rigidly fixed to the extent that they maintain their coordinate position within the matrix. It is to be understood that even though a nucleic acid molecule may be covalently attached to the three dimensional matrix material, the nucleic acid molecule itself may be capable of movement though bound to the matrix, such as for example, when a nucleic acid sequence is bound to the matrix at a single location on the nucleic acid.

According to one aspect, the three dimensional matrix including nucleic acids is porous. According to one aspect, the three dimensional matrix including nucleic acids is porous to the extent that reagents typically used in amplification methods can diffuse or otherwise move through the matrix to contact nucleic acids and thereby amplify nucleic acids under suitable conditions.

According to one aspect, the three dimensional matrix material is chemically inert and thermally stable to allow for various reaction conditions and reaction temperatures. According to this aspect, the three dimensional matrix material is chemically inert and thermally stable to conditions used in amplification and sequencing methods known to those of skill in the art.

According to one aspect, the three dimensional matrix material is optically transparent. According to one aspect, the three dimensional matrix material is optically transparent to allow for three dimensional imaging techniques known to those of skill in the art.

According to one aspect, the nucleic acids are amplified to an extent to produce sufficient levels of amplicons for three dimensional imaging. For example, the nucleic acids are amplified and include a label sufficient for a high level of fluorescence compatible with three dimensional imaging.

According to one aspect, the material used to form the matrix is compatible with a wide range of biological and non-biological specimens in situ so as to avoid extracting the nucleic acid molecules away from their native environment.

According to one aspect, the matrix material may be a semi-solid medium that can be made from polyacrylamide, cellulose, alginate, polyamide, cross-linked agarose, cross-linked dextran or cross-linked polyethylene glycol. In certain aspects, the semi-solid medium has x, y and z axes, and the nucleic acids are present randomly or non-randomly within the three dimensional matrix.

According to one aspect, the matrix material is porous. Porosity can result from polymerization and/or crosslinking of molecules used to make the matrix material. The diffusion property within the gel matrix is largely a function of the pore size. The molecular sieve size is chosen to allow for rapid diffusion of enzymes, oligonucleotides, formamide and other buffers used for amplification and sequencing (>50-nm). The molecular sieve size is also chosen so that large DNA or RNA amplicons do not readily diffuse within the matrix (<500-nm). The porosity is controlled by changing the cross-linking density, the chain lengths and the percentage of co-polymerized branching monomers according to methods known to those of skill in the art.

In certain aspects, the semi-solid medium can be attached to a solid support such as a microscope slide or a flow cell. The solid support can be attached to the bottom surface of the semi-solid medium.

BRIEF DESCRIPTION OF THE DRAWINGS

The foregoing and other features and advantages of the present invention will be more fully understood from the following detailed description of illustrative embodiments taken in conjunction with the accompanying drawings.

FIGS. 7C-E depict DNA amplicons with no shear stress (7C), DNA amplicons with no crosslinking and stretched out from 5 minutes of high shear stress (7D), and DNA amplicons with aminoallyl dUTP cross-linking being morphologically preserved after 5 minutes of high shear stress.

DETAILED DESCRIPTION

Figure 1:
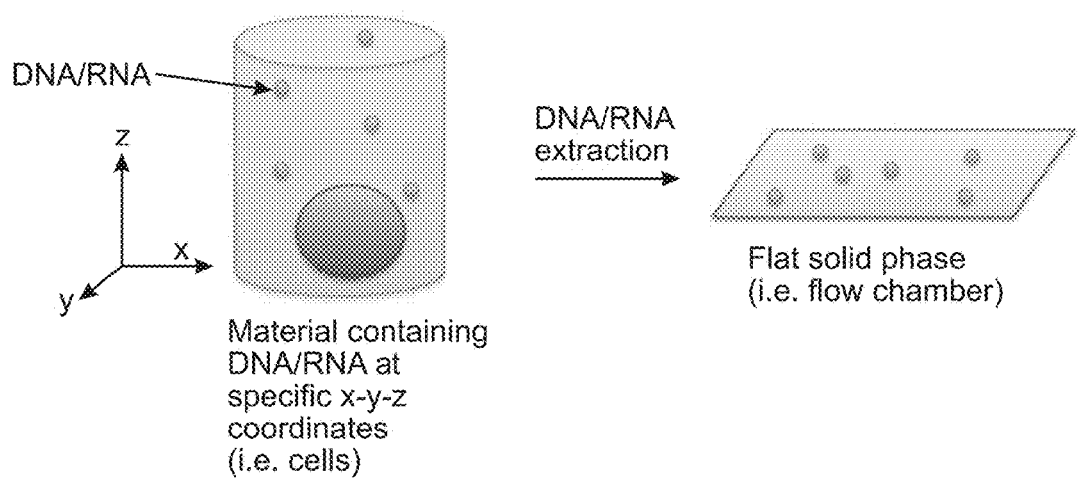
FIG. 1 depicts a schematic of nucleic acids at relative positions within a three dimension environment and extraction and placement onto a two dimensional environment, such as a glass slide or flow chamber.

The present invention provides a three dimensional matrix of a plurality of nucleic acids. The present invention provides a three dimensional matrix including a plurality of nucleic acids bound thereto. According to one aspect, the matrix is a three dimensional nucleic acid-containing polymer. The nucleic acids may be naturally occurring nucleic acids or non-naturally occurring nucleic acids, such as nucleic acids that have been made using synthetic methods. The nucleic acids in the three dimensional matrix may be ordered or unordered. The nucleic acids in the three dimensional matrix may be present in their natural spatial relationship within a cell, tissue or organism. The nucleic acids in the three dimensional matrix may be present in rows and columns within the three dimensional matrix.

According to one aspect, the nucleic acids are modified to incorporate a functional moiety for attachment to the matrix. The functional moiety can be covalently cross-linked, copolymerize with or otherwise non-covalently bound to the matrix. The functional moiety can react with a cross-linker. The functional moiety can be part of a ligand-ligand binding pair. dNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is cross-linked to modified dNTP or dUTP or both. Suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix.

Suitable exemplary spacer moieties include polyethylene glycol, carbon spacers, photo-cleavable spacers and other spacers known to those of skill in the art and the like.

According to one aspect, a matrix-forming material is contacted to a plurality of nucleic acids spatially arrange in three-dimensions relative to one another.

Matrix forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional cross-linkers are then added to allow the formation of a gel matrix. The unincorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

According to one aspect, a matrix-forming material can be used to encapsulate a biological sample, such as a tissue sample. The formalin-fixed embedded tissues on glass slides are incubated with xylene and washed using ethanol to remove the embedding wax. They are then treated with Proteinase K to permeabilized the tissue. A polymerization inducing catalyst, UV or functional cross-linkers are then added to allow the formation of a gel matrix. The unincorporated material is washed out and any remaining functionally reactive group is quenched. Exemplary tissue samples include any tissue samples of interest whether human or non-human. Such tissue samples include those from skin tissue, muscle tissue, bone tissue, organ tissue and the like. Exemplary tissues include human and mouse brain tissue sections, embryo sections, tissue array sections, and whole insect and worm embryos.

The matrix-forming material forms a three dimensional matrix including the plurality of nucleic acids. According to one aspect, the matrix-forming material forms a three dimensional matrix including the plurality of nucleic acids while maintaining the spatial relationship of the nucleic acids. In this aspect, the plurality of nucleic acids are immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise crosslinking with the matrix-forming material. The plurality of nucleic acids may also be immobilized within the matrix by covalent attachment or through ligand-protein interaction to the matrix.

According to one aspect, the matrix is porous thereby allowing the introduction of reagents into the matrix at the site of a nucleic acid for amplification of the nucleic acid. A porous matrix may be made according to methods known to those of skill in the art. In one example, a polyacrylamide gel matrix is co-polymerized with acrydite-modified streptavidin monomers and biotinylated DNA molecules, using a suitable acrylamide:bis-acrylamide ratio to control the cross-linking density. Additional control over the molecular sieve size and density is achieved by adding additional cross-linkers such as functionalized polyethylene glycols. According to one aspect, the nucleic acids, which may represent individual bits of information, are readily accessed by oligonucleotides, such as labeled oligonucleotide probes, primers, enzymes and other reagents with rapid kinetics.

According to one aspect, the matrix is sufficiently optically transparent or otherwise has optical properties suitable for standard Next Generation sequencing chemistries and deep three dimensional imaging for high throughput information readout. The Next Generation sequencing chemistries that utilize fluorescence imaging include ABI SoLiD (Life Technologies), in which a sequencing primer on a template is ligated to a library of fluorescently labeled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The workflow is achieved using an automated fluidics and imaging device (i.e. SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (HiSeq, Illumia).

According to certain aspects, the plurality of nucleic acids may be amplified to produce amplicons by methods known to those of skill in the art. The amplicons may be immobilized within the matrix generally at the location of the nucleic acid being amplified, thereby creating a localized colony of amplicons. The amplicons may be immobilized within the matrix by steric factors. The amplicons may also be immobilized within the matrix by covalent or noncovalent bonding. In this manner, the amplicons may be considered to be attached to the matrix. By being immobilized to the matrix, such as by covalent bonding or crosslinking, the size and spatial relationship of the original amplicons is maintained. By being immobilized to the matrix, such as by covalent bonding or crosslinking, the amplicons are resistant to movement or unraveling under mechanical stress.

According to one aspect, the amplicons, such as DNA amplicons, are then copolymerized and/or covalently attached to the surrounding matrix thereby preserving their spatial relationship and any information inherent thereto. For example, if the amplicons are those generated from DNA or RNA within a cell embedded in the matrix, the amplicons can also be functionalized to form covalent attachment to the matrix preserving their spatial information within the cell thereby providing a subcellular localization distribution pattern.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) Tetrahedron Lett. 22: 1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain embodiments of the invention oligonucleotides and/or polynucleotides may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes.

Nucleic acids may be obtained from libraries, e.g., genomic libraries, cDNA libraries and the like. Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, incorporated herein by reference in their entirety for all purposes.

In certain embodiments, nucleic acids are those found naturally in a biological sample, such as a cell or tissue.

In still other aspects, a matrix is used in conjunction with a solid support. For example the matrix can be polymerized in such a way that one surface of the matrix is attached to a solid support (e.g., a glass surface), while the other surface of the matrix is exposed or sandwiched between two solid supports. According to one aspect, the matrix can be contained within a container.

Solid supports of the invention may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

Embodiments of the present invention are further directed to the amplification of nucleic acid sequences within the matrix, i.e. in situ, within the matrix. Methods of amplifying nucleic acids include rolling circle amplification in situ. In certain aspects, methods of amplifying nucleic acids involves the use of PCR, such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364; incorporated herein by reference in their entirety for all purposes). Alternative amplification methods include: self sustained sequence replication (Guatelli et al. (1990) Proc. Natl. Acad. Sci. USA 87:1874, incorporated herein by reference in its entirety for all purposes), transcriptional amplification system (Kwoh et al. (1989) Proc. Natl. Acad. Sci. US. 86:1173, incorporated herein by reference in its entirety for all purposes), Q-Beta Replicase (Lizardi et al. (1988) BioTechnology 6:1197, incorporated herein by reference in its entirety for all purposes), recursive PCR (Jaffe et al. (2000) J. Biol. Chem. 275:2619; and Williams et al. (2002) J. Biol. Chem. 277:7790; incorporated herein by reference in their entirety for all purposes) or any other nucleic acid amplification method using techniques well known to those of skill in the art. A variety of amplification methods are described in U.S. Pat. Nos. 6,391,544, 6,365,375, 6,294,323, 6,261,797, 6,124,090 and 5,612,199, incorporated herein by reference in their entirety for all purposes.

Embodiments of the present invention are directed to methods of amplifying nucleic acids in situ within the matrix by contacting the nucleic acids within the matrix with reagents and under suitable reaction conditions sufficient to amplify the nucleic acids. According to one aspect, the matrix is porous to allow migration of reagents into the matrix to contact the nucleic acids. In certain aspects, oligonucleotides are amplified by selectively hybridizing an amplification primer to an amplification site at the 3' end of an oligonucleotide using conventional methods. Amplification primers are 6 to 100, and even up to 1,000, nucleotides in length, but typically from 10 to 40 nucleotides, although oligonucleotides of different length are of use. Amplification primers may be present in solution to be added to the matrix or they may be added during formation of the matrix to be present therein sufficiently adjacent to nucleic acids to allow for hybridization and amplification.

Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanehisa, M., 1984, Nucleic Acids Res. 12: 203, incorporated herein by reference in its entirety for all purposes.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher Tm than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in Current Protocols in Molecular Biology, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) Nucleic Acids Res. 30:e43, and Rouillard et al. (2004) Nucleic Acids Res. 32:W176, incorporated by reference herein in their entirety for all purposes).

In accordance with certain examples, methods of sequencing nucleic acid in situ within a matrix are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use with the matrix in which the nucleic acids are present. Reversible termination methods use step-wise sequencing-by-synthesis biochemistry that coupled with reversible termination and removable fluorescence (Shendure et al. supra ands U.S. Pat. Nos. 5,750,341 and 6,306,597, incorporated herein by reference. FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes. Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes. MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes.

According to certain aspects, the nucleic acids within the matrix can be interrogated using methods known to those of skill in the art including fluorescently labeled oligonucleotide/DNA/RNA hybridization, primer extension with labeled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

According to one aspect, methods described herein produce a three dimensional nucleic acid amplicon matrix which is stable, long-lasting and resistant, substantially resistant or partially resistant to enzymatic or chemical degradation. The three dimensional nucleic acid amplicon matrix can be repeatedly interrogated using standard probe hybridization and/or fluorescence based sequencing. The three dimensional nucleic acid amplicon matrix can be repeatedly interrogated with little or no signal degradation, such as after more than 50 cycles, and with little position shift, such as less than 1 μm per amplicon.

According to one aspect, a plurality of circular DNA molecules are covalently linked to one another. The circular DNA molecules are then amplified using methods known to those of skill in the art, such as isothermal enzymatic amplification one example of which is rolling circle amplification. According to this aspect, the amplicons are localized near the circular DNA. According to this aspect, the amplicons form a shell around the circular DNA or otherwise assemble around the circular DNA. Each circular DNA may have more than 1000 amplicons surrounding or otherwise associated therewith. According to this aspect, the amplicons surrounding a particular circular DNA provide a high signal intensity, due in part to the number of amplicons and/or detectable labels associated with the amplicons. The amplicons may be functionalized and cross-linked or otherwise covalently bound together around their associate circular DNA to form a series or network of tightly bound DNA amplicon shells around each circular DNA. The series or network of tightly bound DNA amplicon shells around each circular DNA may be assembled onto a three-dimensional support. According to one aspect, the series or network of tightly bound DNA amplicon shells around each circular DNA may be assembled onto a three-dimensional support producing a three dimensional DNA polymer with defined overall shape, size and amplicon position.

According to one aspect, amplicons are covalently linked without the need for separate cross-linkers, such as bis-N-succinimidyl-(nonaethylene glycol) ester. An acrydite moiety, such as a catalyst activated acrydite moiety is introduced at the end of a long carbon spacer (i.e., about C6 to about C12) at position 5 of a uracil base a representative formula of which is shown below.

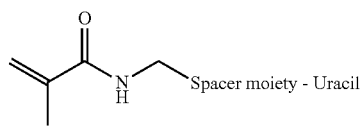

In the formula below, R represents the acrydite spacer moiety attached to the 5 position of the uracil base.

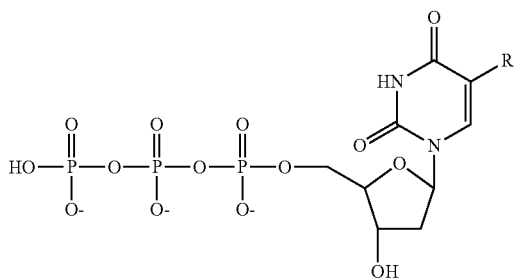

When copolymerized with bis-acrylamide in the presence of a catalyst, a polymerization reaction takes place, encapsulating the circular DNA with the amplicons and fixing the amplicons in position. The chemically inert nature of the polymerized mixture allows various downstream applications. The spacer can be a carbon chain of between about 2 carbons to about 200 carbons. The spacer can be polyethylene glycol. The length of the spacer can vary from about 30 angstroms to about 100 angstroms and can be of various molecular weights. The spacer can be permanent or reversible, such as by using UV light, enzymes, chemical cleavage, etc. A three dimensional matrix, such as a polyacrylamide gel matrix, can be used to embed a variety of biological structures containing enzymatically or chemically modified DNA or RNA molecules containing an acrydite functional moiety or moieties. The non-nucleic acid component is selectively dissolved using detergents, proteases, organic solvents or denaturants to create a three dimensional matrix that preserves individual DNA or RNA molecules and their relative spatial location. Examples include embedding cells, healthy and diseased tissues and tissue sections, small model organisms such as worms and insects, bacterial colonies or biofilm, environmental samples containing other DNA or RNA containing materials or organisms.

This invention is further illustrated by the following examples, which should not be construed as limiting. The contents of all references, patents and published patent applications cited throughout this application are hereby incorporated by reference in their entirety for all purposes.

EXAMPLE I

Immobilizing, Amplifying and Imaging DNA/RNA Molecules Within Cells

Human iPS cells or human primary fibroblasts are grown on a 1.5 cover slip. They are fixed using 4% formaldehyde in PBS for 15 min, followed by three washes of 70% ethanol. The reverse transcription mixture containing 1 uM random hexamer or 0.1 uM polydT(18)V primer with additional adapter sequences (TCTCGGGAACGCTGAAGA), 250 uM dNTP, 40 uM aminoallyl dUTP (Anaspec), 20U RNase inhibitor and 100 U MMuLV reverse transcriptase (Enzymatics) are then added to the fixed cells and incubated overnight at 37° C. The sample is then washed using PBS, and cross-linked using 100 uM BS(PEG)9 (Thermo-Fisher Scientific) in PBS for 1 hour, followed by 1M Tris treatment for 15 min. The circularization mixture containing 25U CircLigase (Epicentre), 1 mM MnCl and 1 M Betain is added, and the sample is incubated at 60° C. for 2 hours. The residual RNA is degraded using a mixture of RNase cocktail (Roche) and RNase H (Enzymatics) at 37° C. for 1 hour. The RCA primer is then hybridized to the sample at 60° C. for 15 min and washed. For rolling circle amplification, 100 U phi29 DNA polymerase (Enzymatics), 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently label oligonucleotides are diluted in 2×SSC and hybridized to the matrix containing the DNA amplicons at 60° C. and washed. Imaging is done using Leica SP5 scanning confocal microscope using 10×, 20× or 63× objectives in four color channels (FITC, Cy3, Texas Red and Cy5). The image stacks containing up to 50 optical sections are then visualized using Imaris Bitplane software for three dimensional reconstruction of the DNA amplicons within the sample matrix.

Figure 2:
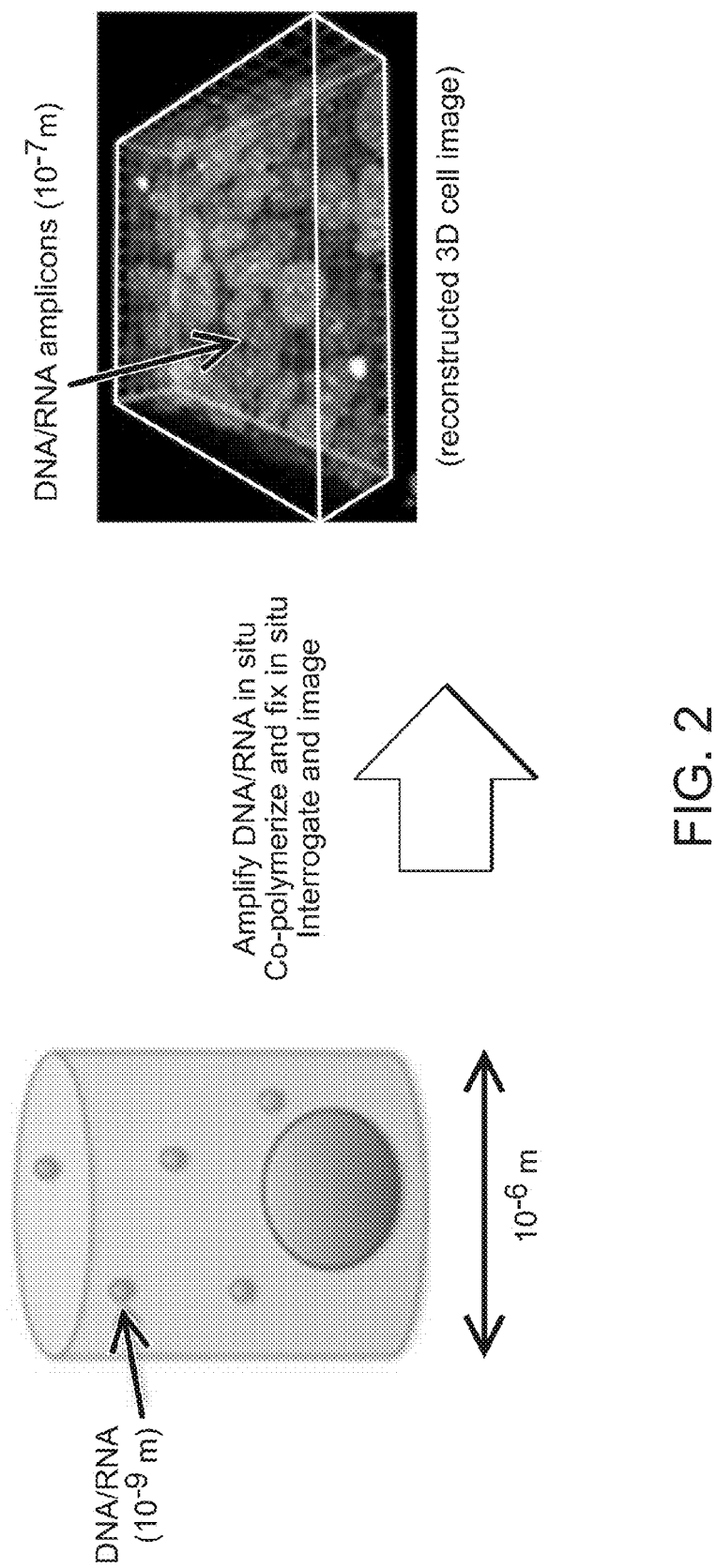
FIG. 2 depicts in schematic the process of creating a matrix of nucleic acids within cells in situ, followed by amplifying the nucleic acids, such as DNA or RNA, in situ, co-polymerizing the amplicons in situ, covalently attaching the amplicons to the matrix material, interrogating the amplicons and imaging the amplicons along with a reconstructed 3D cell image with DNA/RNA amplicons on the order of 10−7 m.

Methods described herein allow one to immobilize, amplify and image single DNA/RNA molecules in a three dimensional space without perturbing the structure. As shown in FIG. 2, single cells were grown in tissue culture. DNA/RNA was amplified in situ. The DNA/RNA was co-polymerized into a matrix material in situ, and individual amplicons were interrogated/hybridized with fluorescent oligonucleotides and imaged. When viewed under much higher magnification, individual amplicons can be imaged using confocal microscopy. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

According to one specific aspect, inside individual mammalian cells, 20 to 500K mRNA molecules are distributed throughput the cytoplasm (Islam et al., 2011). According to embodiment, cells are fixed and permeabilized. Cellular RNA is then converted into cDNA molecules using dUTP in place or in addition to dTTP. The cDNA molecules containing modified dUMP residues are then cross-linked to each other and circularized, forming a three dimensional pseudopolymer of circular cDNA molecules inside individual cells. Then rolling circle amplification is used to amplify the cDNA network into a DNA amplicon network. This cell-based DNA amplicon network then stores information about each transcript's identity, location, variation/mutations, etc. The cell-based DNA amplicon matrix can be read using sequencing by ligation (i.e. ABI SoLiD), sequencing by synthesis (i.e. Illumina), or any other proprietary or open sequencing chemistries (see Drmanac et al., 2010; Shendure et al., 2005 herein incorporated by reference in their entireties). Given the three dimensional nature of the DNA amplicon network, one can use confocal or multi-photon microscopy to sequencing individual amplicons throughout the whole thickness of the amplicon network, enabling one to visualize the cDNA distribution of transcripts between the apical side and the basal side of the cells as shown in FIG. 2. Given the tight packing density, one can selectively read different subpopulations sequentially, reducing the density of information read at any given time and extending over time for better spatial resolution.

EXAMPLE II

Immobilizing, Amplifying and Imaging DNA/RNA Molecules Within a Fly Embryo

*Drosophila* embryos are fixed using 4% formaldehyde in PBS, followed by multiple washes of 70% ethanol. The embryos are then mounted on a cover glass using an optically transparent adhesive. The reverse transcription mixture containing 1 uM random hexamer or 0.1 uM polydT(18)V primer with additional adapter sequences (TCTCGGGAACGCTGAAGA), 250 uM dNTP, 40 uM aminoallyl dUTP (Anaspec), 20U RNase inhibitor and 100 U MMuLV reverse transcriptase (Enzymatics) are then added to the fixed cells and incubated overnight at 37° C. The sample is then washed using PBS, and cross-linked using 100 uM BS(PEG)9 (Thermo-Fisher Scientific) in PBS for 1 hour, followed by 1M Tris treatment for 15 min. The circularization mixture containing 25U CircLigase (Epicentre), 1 mM MnCl and 1 M Betain is added, and the sample is incubated at 60° C. for 2 hours. The residual RNA is degraded using a mixture of RNase cocktail (Roche) and RNase H (Enzymatics) at 37° C. for 1 hour. The RCA primer is then hybridized to the sample at 60° C. for 15 min and washed. For rolling circle amplification, 100 U phi29 DNA polymerase (Enzymatics), 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently label oligonucleotides are diluted in 2×SSC and hybridized to the matrix containing the DNA amplicons at 60° C. and washed. Imaging is done using Leica SP5 scanning confocal microscope using 10×, 20× or 63× objectives in four color channels (FITC, Cy3, Texas Red and Cy5). The image stacks are then visualized using Imaris Bitplane software for three dimensional reconstruction of the DNA amplicons within the sample matrix.

As shown in FIG. 2, fly embryos were obtained and DNA/RNA was amplified in situ. The DNA/RNA was copolymerized into a matrix material in situ, and individual amplicons were interrogated/hybridized with fluorescent oligonucleotides and imaged. When viewed under much higher magnification, individual amplicons can be imaged using confocal microscopy even in these thick biological specimens. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

EXAMPLE III

Immobilizing, Amplifying and Imaging DNA/RNA Molecules Within Mouse Brain

A fresh frozen adult mouse brain sections (20-um cryosections) are fixed using 4% formaldehyde in PBS. It is then treated with 0.4 ug/ml Proteinase K for 30 min at room temperature and thoroughly washed using 70%, 95% and 100% ethanol. The reverse transcription mixture containing 1 uM random hexamer or 0.1 uM polydT(18)V primer with additional adapter sequences (TCTCGGGAACGCT-GAAGA), 250 uM dNTP, 40 uM aminoallyl dUTP (Anaspec), 20U RNase inhibitor and 100 U MMuLV reverse transcriptase (Enzymatics) are then added to the fixed cells and incubated overnight at 37° C. The sample is then washed using PBS, and cross-linked using 100 uM BS(PEG)9 (Thermo-Fisher Scientific) in PBS for 1 hour, followed by 1M Tris treatment for 15 min. The circularization mixture containing 25U CircLigase (Epicentre), 1 mM MnCl and 1 M Betain is added, and the sample is incubated at 60° C. for 2 hours. The residual RNA is degraded using a mixture of RNase cocktail (Roche) and RNase H (Enzymatics) at 37° C. for 1 hour. The RCA primer is then hybridized to the sample at 60° C. for 15 min and washed. For rolling circle amplification, 100 U phi29 DNA polymerase (Enzymatics), 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently label oligonucleotides are diluted in 2×SSC and hybridized to the matrix containing the DNA amplicons at 60° C. and washed. Imaging is done using Leica epifluorescence microscope using a 10× objective in four color channels (FITC, Cy3, Texas Red and Cy5) in a tiled scan mode (20 by 15 separate images). The images are then stitched together during the image acquisition and visualized using Imaris Bitplane software.

As shown in FIG. 2, mouse brain sections were obtained and DNA/RNA was amplified in situ. The DNA/RNA was copolymerized into a matrix material in situ, and individual amplicons were interrogated/hybridized with fluorescent oligonucleotides and imaged. When viewed under much higher magnification, individual amplicons can be imaged using confocal microscopy even in these thick biological specimens. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

EXAMPLE IV

Crosslinking of Amplicons

A 50-base oligonucleotide is phosphorylated at the 5' end using polynucleotide kinase in the T4 ligase buffer for 15 min. The reaction mixture is incubated with CircLigase mixture at 60° C. for 1 hour to generate circular templates for testing. The RCA primer (18 bases) is then hybridized to the circular template in solution and a diluted template: primer mixture is used for rolling circle amplification. The RCA reaction solution contained 0, 0.1 uM, 1 uM or 10 uM aminoallyl dUTP in addition to the normal dNTP. The reaction mixture was then loaded onto an 1% agarose gel and visualized using SYBR safe dyes.

Figure 3:
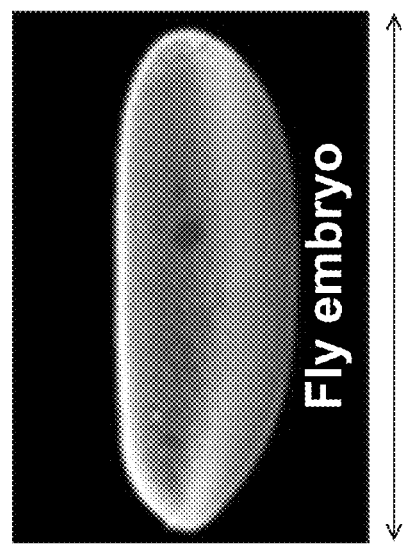
FIG. 3 is an image of a whole mount Drosophilia embryo.

The incorporation of aminoallyl dUTP that is later cross-linked to each other and to the amine exposing substrate still allows for reverse transcription using M-MuLV reverse transcriptase and rolling circle amplification using Phi29 DNA polymerase, albeit at a reduced rate in a concentration dependent manner. Increasing amounts of aminoallyl dUTP were added as a competitor to dTTP present in the amplification mixture in solution. The rolling circle amplicons are single stranded DNA which are highly folded. As shown in FIG. 3A, these structures run as a single large band around ~10-15-kb on an 1% agarose gel.

EXAMPLE V

The Incorporation of Aminoallyl dUTP Leads to Slightly Smaller Diameter of the Average DNA Amplicon Size A 50-base oligonucleotide is phosphorylated at the 5' end using polynucleotide kinase in the T4 ligase buffer for 15 min. The reaction mixture is incubated with CircLigase mixture at 60° C. for 1 hour to generate circular templates for testing. The RCA primer (18 bases) is then hybridized to the circular template in solution and a diluted template: primer mixture is used for rolling circle amplification. The RCA reaction solution contained aminoallyl dUTP and normal dNTP at varying ratios (1:50 to 1:50,000). After 8 hours of RCA, the reaction mixture was diluted in PBS and bound to amino-silane treated coverglass. The bound RCA amplicons were then visualized by staining it with SYBR safe and imaging it using an epifluorescence microscope (63× objective). The images were then processed using Imaris Bitplane to identify individual amplicons and measure the average diameter of each spot.

The incorporation of aminoallyl dUTP leads to slightly smaller diameter of the average DNA amplicon size. The circular cDNA template was used for rolling circle amplification, during which a range of aminoallyl dUTP was added. The amplicon mixture in solution was then arrayed on a glass surface and hybridized to a common fluorescent probe sequence. Since aminoallyl dUTP has a single positive charge, the increasing incorporation of aminoallyl dUTP led to a reduction in the overall negative charge, making each DNA amplicon slightly more compact. As shown in FIG. 3B, the ratio shown in the graph legend represents the molar ratio of aminoallyl dUTP to dTTP during the amplification step.

EXAMPLE VI

Aminoallyl dUTP Cross-Linking Preserves DNA Amplicons

A 50-base oligonucleotide is phosphorylated at the 5' end using polynucleotide kinase in the T4 ligase buffer for 15 min. The reaction mixture is incubated with CircLigase mixture at 60° C. for 1 hour to generate circular templates for testing. The RCA primer (18 bases) is then hybridized to the circular template in solution and a diluted template: primer mixture is used for rolling circle amplification with or without aminoallyl dUTP. After 8 hours of RCA, the reaction mixture was diluted in PBS and bound to amino-silane treated coverglass. The bound RCA amplicons were then cross-linked with BS(PEG)9. They were then washed using a continuous stream of 2×SSC wash solution for 1 min, stained with SYBR safe and imaged using an epifluorescence microscope (63× objective).

The DNA amplicons generated in solution are arrayed on a glass surface and cross-linked via the aminoallyl moiety. They were then exposed to a constant flow of distilled water running across its surface with and with the cross-linker chemistry for 5 min at room temperature and then imaged after SYBR Gold staining. As shown in FIG. 3C, the DNA amplicons that were not cross-linked stretched out as a result of high shear stress for about 5 minutes. The DNA amplicons cross-linked with aminoallyl dUTP were morphologically preserved after high shear stress for 5 minutes.

EXAMPLE VII

DNA Amplicons in Human Fibroblasts are Structurally and Chemically Stable

Human primary fibroblasts are grown on a 1.5 cover slip. They are fixed using 4% formaldehyde in PBS for 15 min, followed by three washes of 70% ethanol. The reverse transcription mixture containing 1 uM random hexamer or 0.1 uM polydT(18)V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS(PEG)9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM amino-allyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed. Imaging is done using Leica SP5 scanning confocal microscope using a 63× objectives. The fluorescent oligonucleotides are stripped off using 80% formamide heated to 80° C. The sample is then dried and stored at 4° C. from July 2011 to March 2012. The sample was rehydrated in PBS, and rehybridized to the fluorescently labeled oligonucleotides and imaged. The second image was obtained using an epifluorescence microscope.

Figure 4:
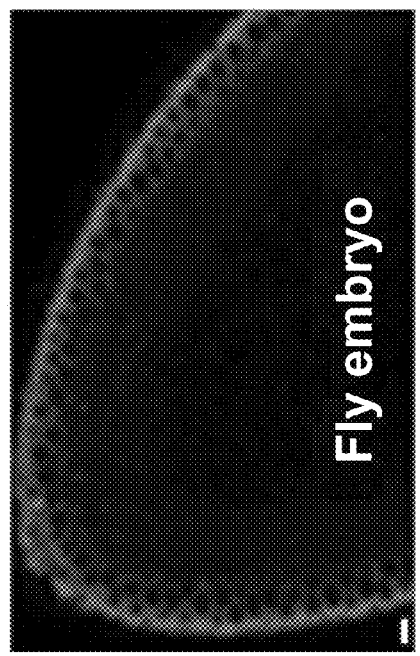
FIG. 4 is an optical section of a fly embryo.

The DNA amplicons are structurally and chemically stable over a long period of time once cross-linked. As shown in FIG. 4A, the DNA amplicons preserved as a three dimensional matrix in human fibroblasts can be interrogated using fluorescent primers and stored in phosphate buffered solution for up to a year and re-interrogated without losing their structural or sequence information. The different image quality here reflects the difference between confocal microscopy vs. epifluorescence microscopy, not the sample quality.

EXAMPLE VIII

A DNA Amplicon Matrix Within a Cell is Structurally and Chemically Stable

Human primary fibroblasts are grown on a 1.5 cover slip. They are fixed using 4% formaldehyde in PBS for 15 min, followed by three washes of 70% ethanol. The reverse transcription mixture containing 1 uM random hexamer or 0.1 uM polydT(18)V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS(PEG)9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed. Imaging is done using Leica SP5 scanning confocal microscope using a 63× objectives. The fluorescent oligonucleotides are stripped off using 80% formamide heated to 80° C. The sample is then washed with distilled waterand rehybridized to the fluorescently labeled oligonucleotides and imaged.

As shown in FIG. 4B, the DNA amplicon matrix inside the cell can be stripped using harsh chemical agents (i.e. 0.1N NaOH, 80% formamide) and heated up to 95° C. for a prolonged period of time without losing their structural integrity or definition.

EXAMPLE IX

A DNA Amplicon Matrix Within a Cell is Structurally and Chemically Stable

Human iPS cells are grown on a 1.5 cover slip. They are fixed using 4% formaldehyde in PBS for 15 min, followed by three washes of 70% ethanol. The reverse transcription mixture containing 1 uM random hexamer or 0.1 uM polydT(18)V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS(PEG)9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed three times using 2×SSC. After imaging, the fluorescent oligonucleotides are stripped off using 80% formamide heated to 80° C. The sample is then washed with distilled water and rehybridized to the fluorescently labeled oligonucleotides. This cycle is repeated sixty times (5 minutes per cycle). The multiple images were then aligned and processed using MatLab to identify a region of interest. Up to twenty single cells and amplicons within the cells were chosen and compared to the cell-free region for determining the signal to noise ratio after each hybridization and stripping cycle. The sample was then used for 12 cycles of sequencing by ligation. After sequencing, the 12 image stacks (19 optical sections per field) were analyzed on Imaris Bitplane and individual DNA amplicons were tracked over the whole sequencing run. Only those amplicons that were identified in all 12 cycles were analyzed.

As shown in FIG. 4C, the sample can be cycled through more than 50 heating, cooling, enzymatic and chemical reactions without any changes in the signal to noise ratio. The high absolute signal intensity here was due to insufficient probe washing in the initial cycles. When the individual DNA amplicons in the matrix was imaged in three dimensions using confocal microscopy and tracked over 12 cycles, one measure the relative displacement of each amplicon over time. Despite numerous thermal, chemical and enzymatic manipulations, the mean displacement of each amplicon was ~500-nm in both lateral and axial dimensions, which was about the diameter of each amplicon. An example image of the analysis is shown in the right panel, in which the line representing the displacement is shown in different colors according to their cycle number.

EXAMPLE X

DNA Amplicons Embedded Within a Cross-Linked Matrix in a Cell are Imaged

Human iPS cells are grown on a 1.5 cover slip. They are fixed using 4% formaldehyde in PBS for 15 min, followed by three washes of 70% ethanol. The reverse transcription mixture containing 1 uM random hexamer or 0.1 uM polydT(18)V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS(PEG)9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed three times using 2×SSC. Leica SP5 scanning confocal microscope with 63× objective is used and scanning optical zoom of 5× is used. The line scan was repeated three times and averaged to generate a high quality image.

Figure 5:
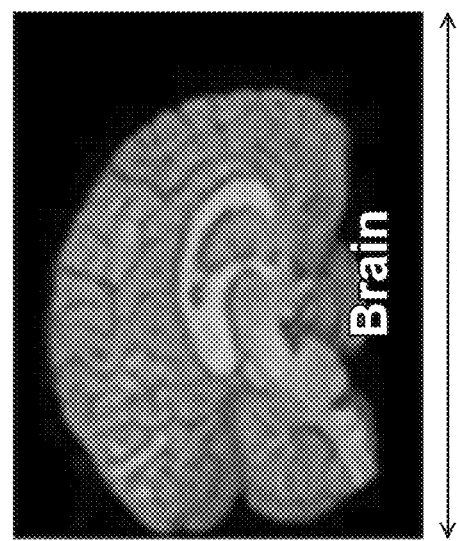
FIG. 5 is an image of a whole mount mouse brain section.
Figure 7A:
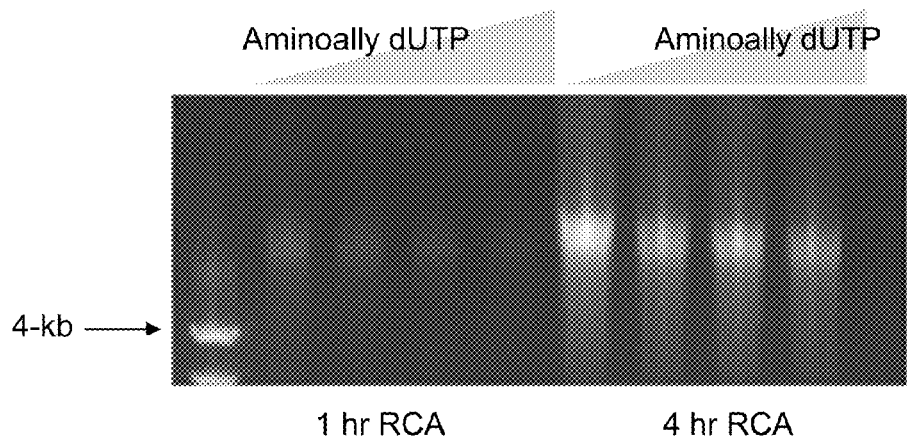
FIG. 7A is a gel image of aminoallyl dUTP after 1 hour of rolling circle amplification and after 4 hours of rolling circle amplification
Figure 7B:
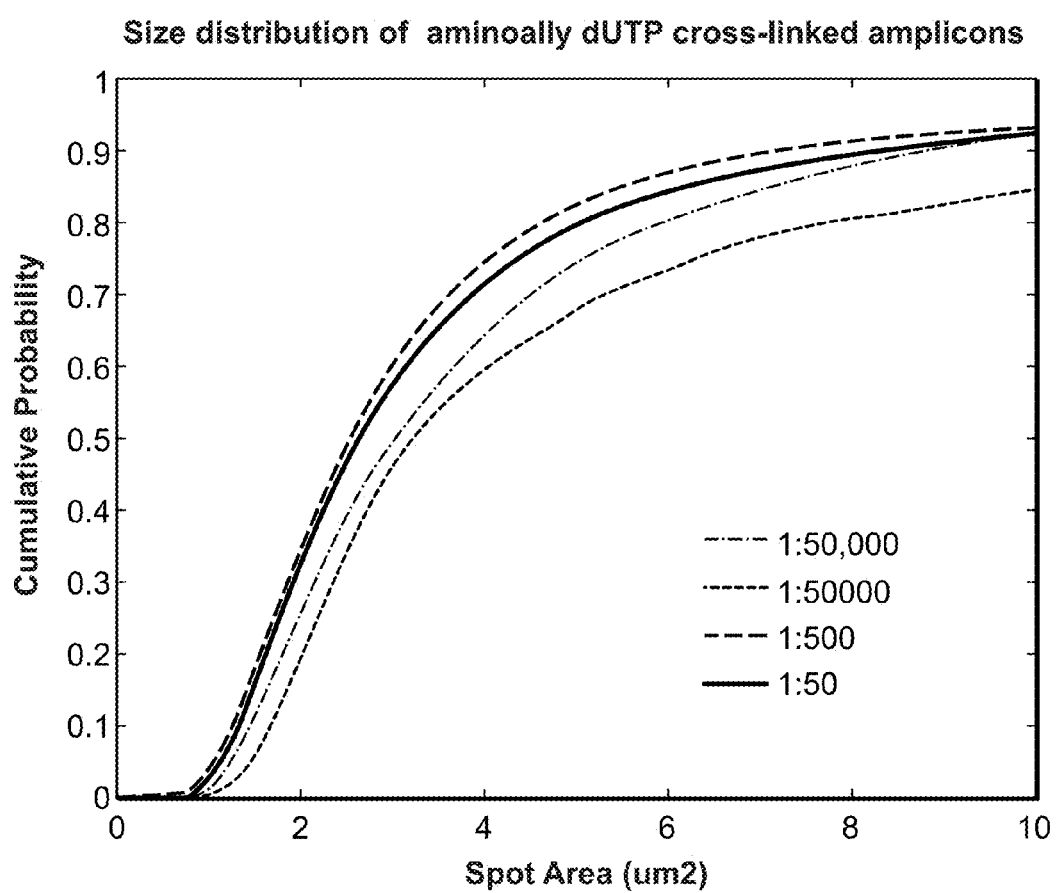
FIG. 7B is a graph representative of the molar ratio of aminoallyl dUTP to dTTP during amplification.
Figure 8A:
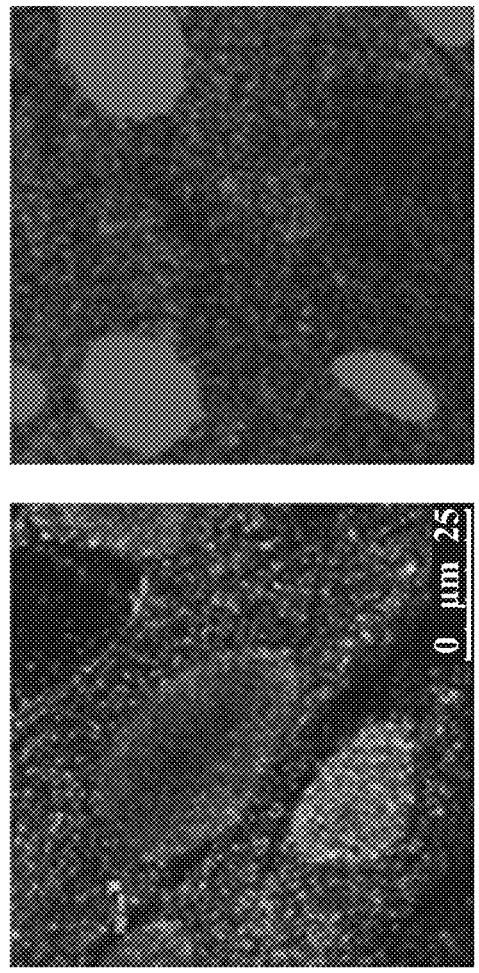
FIG. 8A depicts DNA amplicons cross-linked in fibroblasts.
Figure 8B:
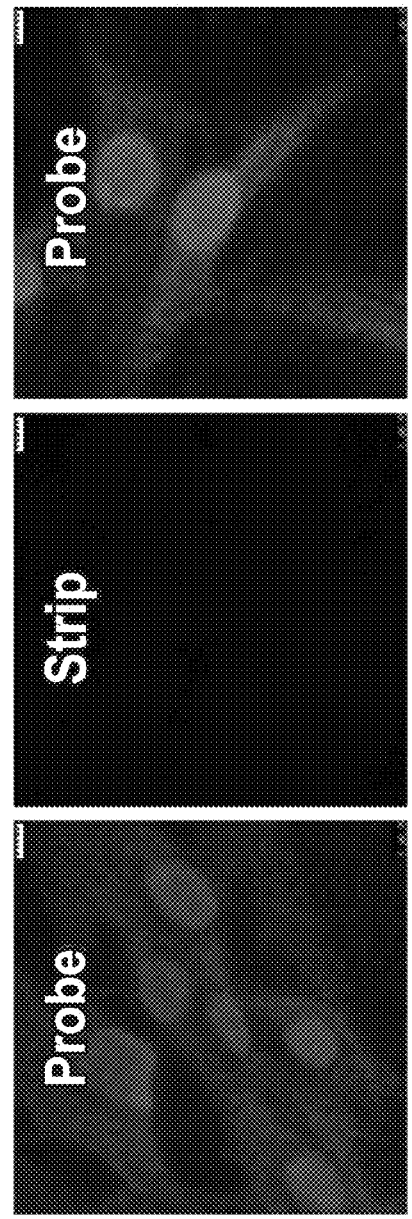
FIG. 8B depicts the results of experiments demonstrating structural integrity of a DNA amplicon matrix within a cell.
Figure 8C:
FIG. 8C depicts the results of experiments demonstrating structural integrity of a DNA amplicon matrix within a cell after numerous chemical reactions.
Figure 8C:
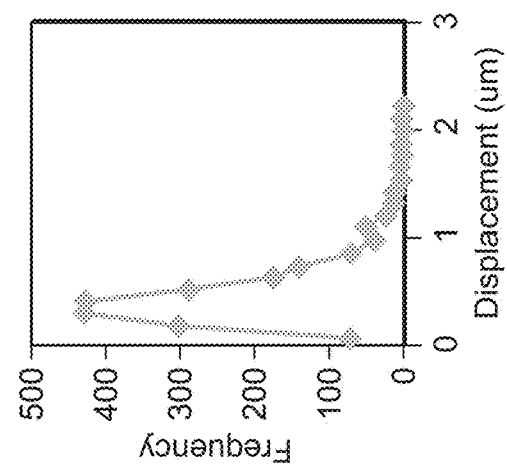
Figure 8C:
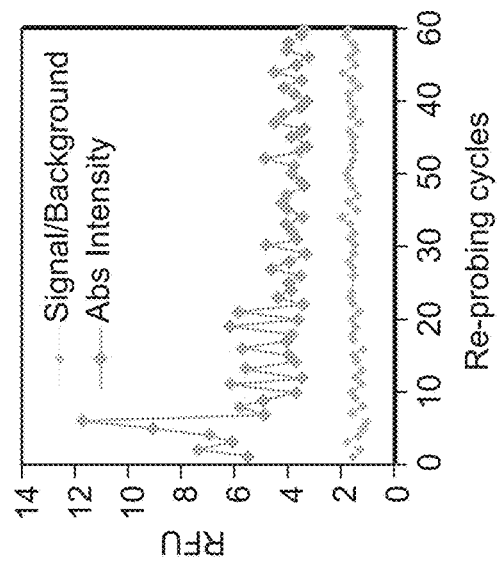
Figure 9A:
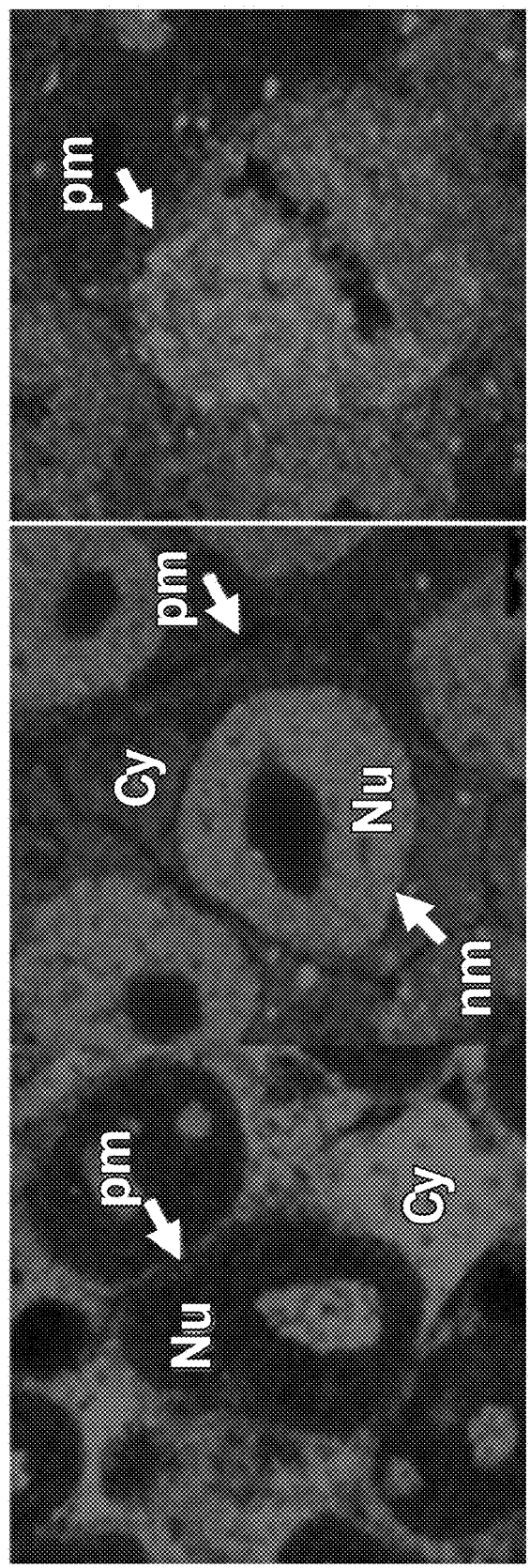
FIG. 9A depicts amplicons within pluripotent stem cells.
Figure 9B:
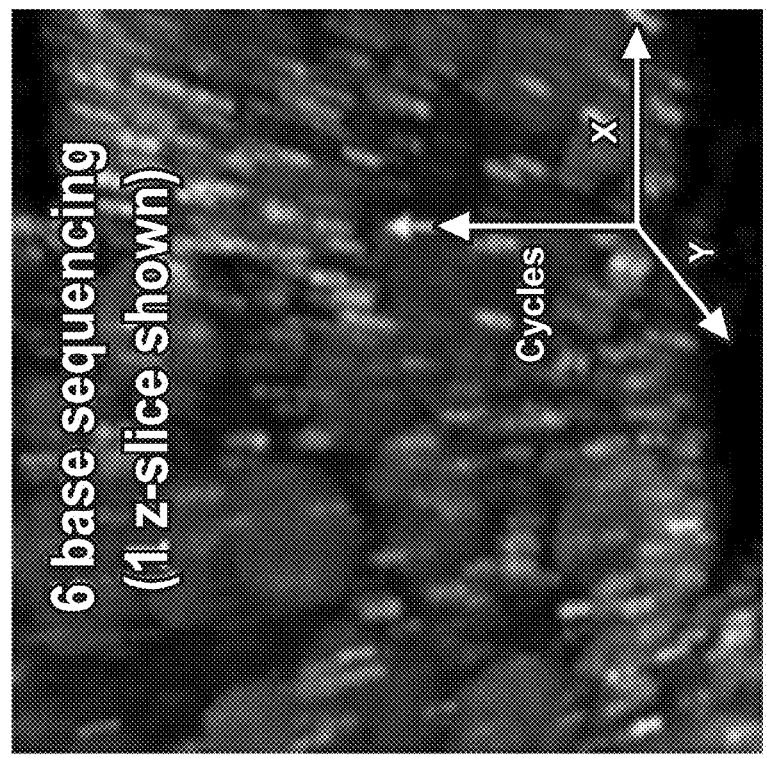
FIG. 9B depicts confocal microscope images of cells with amplicons being sequenced.
Figure 9B:
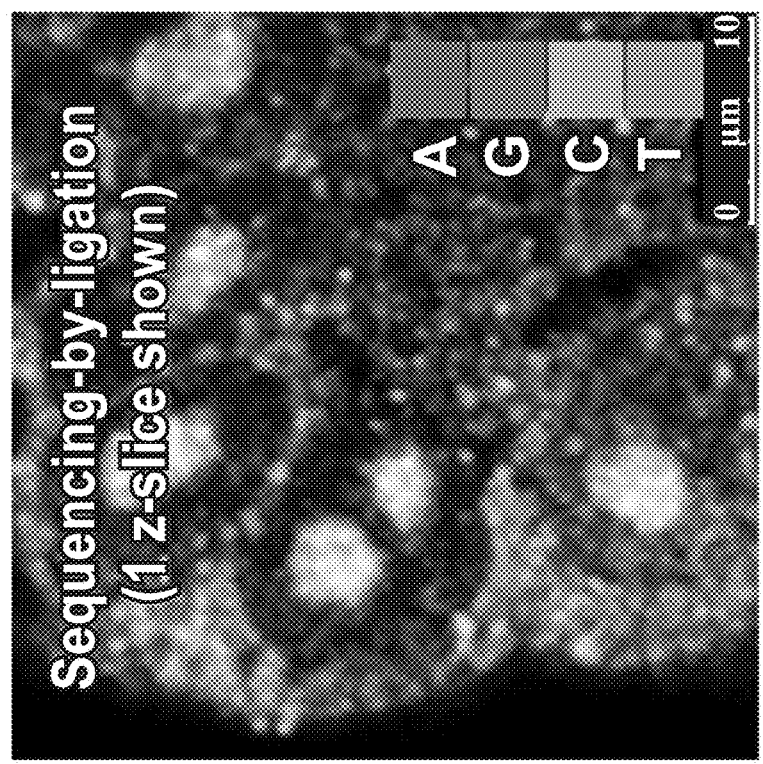
Figure 10:
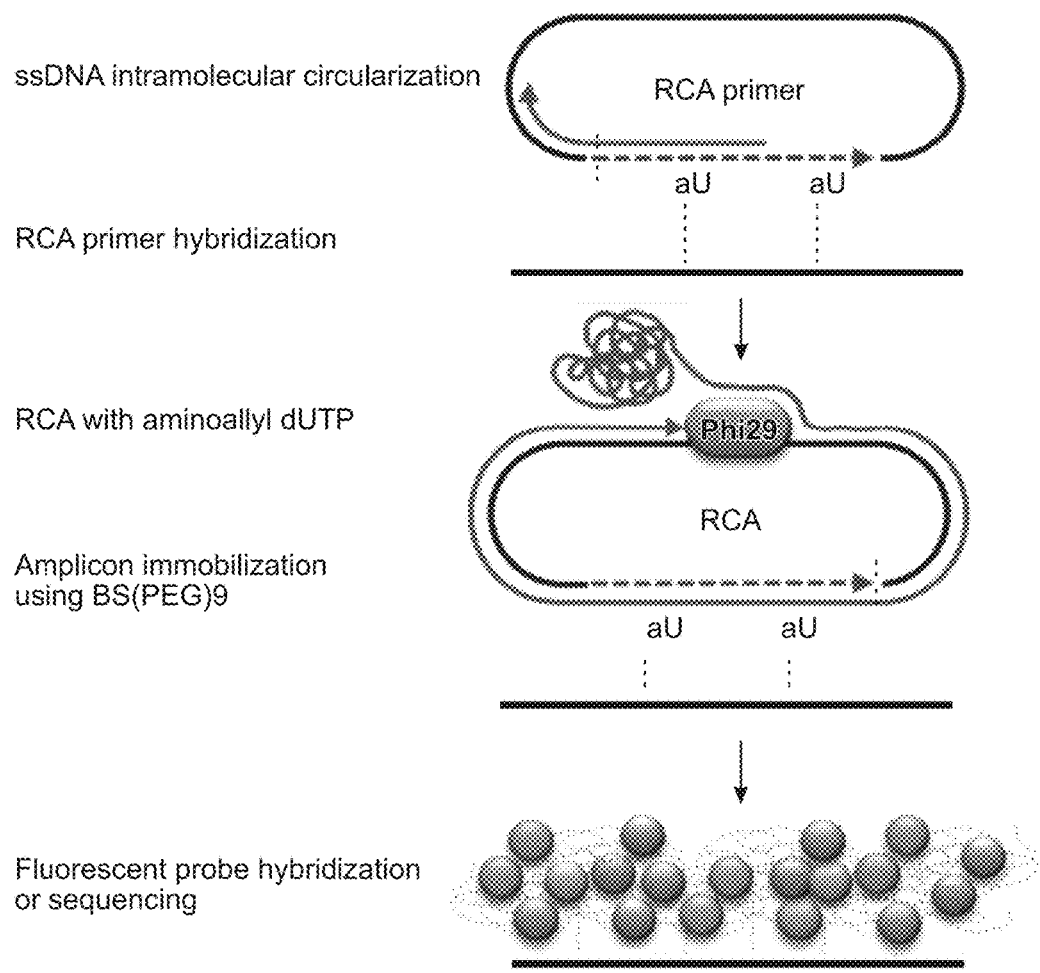
FIG. 10 depicts in schematic a process for crosslinking or copolymerizing circular DNA, amplifying the circular DNA to produce amplicons and then placing the DNA amplicons into an ordered 3D matrix using a suitable scaffold material with addressable primers that can serve as amplification primers.

FIG. 5A is an image of the DNA amplicons (derived from reverse transcription of the cytoplasmic and the nuclear RNA) embedded within the cross-linked matrix inside human induced pluripotent stem cells. Individual amplicons are too tightly packed to visualize discrete amplicons, given the optical diffraction limitation in microscopy. But various subcellular compartments where the RNA is not expected to be present (i.e. nm: nuclear membrane, pm: plasma membrane) show dark staining, whereas the nucleus (Nu) and the cytoplasm (Cy) show a high density of the amplicons. The distribution of the cellular RNA show unique patterns from cell to cell (1st panel vs. 2nd panel) and from one cell cycle phase to another (1st panel vs. 3rd panel). These results show that the DNA amplicons can be immobilized, amplified and interrogated in a manner to reflect their original spatial information.

EXAMPLE XI

DNA Amplicons Embedded Within a Cross-Linked Matrix in a Cell are Sequenced

Human iPS cells are grown on a 1.5 cover slip. They are fixed using 4% formaldehyde in PBS for 15 min, followed by three washes of 70% ethanol. The reverse transcription mixture containing 1 uM random hexamer or 0.1 uM polydT (18)V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS(PEG)9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS(PEG)9 in PBS for 1 hour, followed by 1M Tris treatment for 15 min. The sequencing primer is designed with different 3' ends that that each primer can detect only ¼th of the amplicons. If different dinucleotides are added to the 3' ends of the primer, each primer can detect only 1/16th of the amplicons. A chosen sequencing primer in 2×SSC is hybridized to the sample at 60° C. for 15 minutes and washed. A ligation mixture containing 10 U T4 DNA ligase, ligation buffer and 1 uM fluorescently labeled nonamers (a pool containing A, G, C or T at fixed positions and labeled with FITC, Cy3, Texas Red or Cy5, respectively) is added and incubated for 50 min at room temperature. After washing three times with 2×SSC, the cell is imaged on Leica SP5 scanning confocal microscope using four color channels. After imaging, the probe complex is stripped using 80% formamide and washed with distilled water. The sequencing by ligation step is repeated using a different nonamer set interrogating the next sequence.

Using selective sequencing primers, only a subset of the total amplicons can be sequenced for better spatial resolution. The left panel shows a subset of randomly primed cDNA amplicons being sequenced on a confocal microscope. The right panel shows GAPDH cDNA amplicons being sequenced over time using confocal microscopy. Only a single optical section is shown here. The axial dimension represents time or sequencing cycle steps.

EXAMPLE XII

Circular DNA is Cross-Linked or Co-Polymerized Into a Matrix and Amplified

Figure 6:
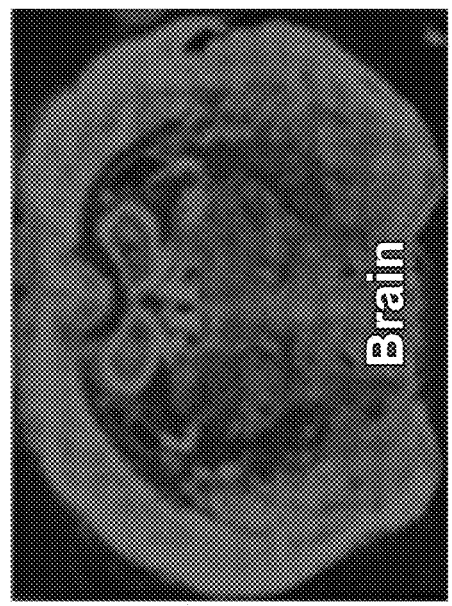
FIG. 6 is an optical section of a mouse brain.

As shown in FIG. 6, circular DNA, including cDNA, is first modified to incorporate a given cross-linker chemistry (i.e. aminoallyl, thiol, biotin) using modified dUTP that competes with natural dTTP. The circular DNA is then cross-linked and/or co-polymerized within a three dimensional container (i.e. cell), conforming the shape and the size of the container. Uncross-linked molecules are then washed away, and one then performs rolling circle amplification, followed by imaging (i.e. sequencing). The density, the size and the signal strength can be controlled by varying the template size, the amplification time and the detection primer sequence. The DNA amplicons can be made into an ordered 3D matrix in a suitable scaffold material with addressable primers that can serve as amplification primers.

EXAMPLE XIII

References

Each reference is incorporated herein by reference in its entirety for all purposes.

Drmanac, R., Sparks, A. B., Callow, M. J., Halpern, A. L., Burns, N. L., Kermani, B. G., Carnevali, P., Nazarenko, I., Nilsen, G. B., Yeung, G., et al. (2010). Human genome sequencing using unchained base reads on self-assembling DNA nanoarrays. Science 327, 78-81.

Islam, S., Kjallquist, U., Moliner, A., Zajac, P., Fan, J. B., Lonnerberg, P., and Linnarsson, S. (2011). Characterization of the single-cell transcriptional landscape by highly multiplex RNA-seq. Genome Res 21, 1160-1167.

Larsson, C., Grundberg, I., Soderberg, O., and Nilsson, M. (2010). In situ detection and genotyping of individual mRNA molecules. Nature methods 7, 395-397.

Larsson, C., Koch, J., Nygren, A., Janssen, G., Raap, A. K., Landegren, U., and Nilsson, M. (2004). In situ genotyping individual DNA molecules by target-primed rolling-circle amplification of padlock probes. Nature methods 1, 227-232.

Shendure, J., Porreca, G. J., Reppas, N. B., Lin, X., McCutcheon, J. P., Rosenbaum, A. M., Wang, M. D., Zhang, K., Mitra, R. D., and Church, G. M. (2005). Accurate multiplex polony sequencing of an evolved bacterial genome. Science 309, 1728-1732.

What is claimed is:

1. A method for nucleic acid sequence identification, comprising
   (a) providing a container comprising a biological sample comprising a first plurality of nucleic acid molecules having a relative three-dimensional spatial relationship that is fixed, wherein said first plurality of nucleic acid molecules is a plurality of ribonucleic acid molecules;
   (b) in said container, contacting said biological sample comprising said first plurality of nucleic acid molecules having said relative three-dimensional spatial relationship that is fixed with matrix-forming material to generate a three-dimensional polymer matrix that encapsulates said first plurality of nucleic acid molecules of said biological sample, wherein said three-dimensional polymer matrix is formed of a material separate from said first plurality of nucleic acid molecules;
   (c) using said first plurality of nucleic acid molecules to generate a second plurality of nucleic acid molecules immobilized to said three-dimensional polymer matrix, which second plurality of nucleic acid molecules have said relative three-dimensional spatial relationship; and
   (d) identifying sequences of said second plurality of nucleic acid molecules while said second plurality of nucleic acid molecules is coupled to said three-dimensional polymer matrix.

2. The method of claim 1, further comprising generating said three-dimensional polymer matrix by polymerizing or cross-linking said matrix-forming material.

3. The method of claim 2, further comprising contacting said first plurality of nucleic acid molecules having said relative three-dimensional spatial relationship within said biological sample with said matrix-forming material.

4. The method of claim 3, further comprising, prior to (a), permeabilizing said biological sample.

5. The method of claim 2, wherein (b) further comprises using a polymerization inducing catalyst, ultraviolet light, or functional cross-linkers to subject said matrix-forming material to polymerization.

6. The method of claim 1, further comprising subjecting said first plurality of nucleic acid molecules to nucleic acid amplification to generate said second plurality of nucleic acid molecules within said three-dimensional polymer matrix.

7. The method of claim 6, wherein said subjecting said first plurality of nucleic acid molecules to said nucleic acid amplification comprises introducing reagents into said three-dimensional polymer matrix.

8. The method of claim 7, wherein said reagents are introduced into said three-dimensional polymer matrix through pores of said three-dimensional polymer matrix.

9. The method of claim 6, further comprising subjecting said second plurality of nucleic acid molecules to conditions sufficient to couple said second plurality of nucleic acid molecules to said three-dimensional polymer matrix.

10. The method of claim 9, wherein said second plurality of nucleic acid molecules couple to said three-dimensional polymer matrix by forming covalent bonds to said three-dimensional polymer matrix.

11. The method of claim 6, further comprising subjecting said second plurality of nucleic acid molecules to conditions sufficient to cross-link said second plurality of nucleic acid molecules to said three-dimensional polymer matrix.

12. The method of claim 6, wherein said nucleic acid amplification comprises rolling circle amplification or comprises use of polymerase chain reaction.

13. The method of claim 1, wherein (d) comprises subjecting said second plurality of nucleic acid molecules or derivatives thereof to sequencing to identify said sequences.

14. The method of claim 13, wherein said sequencing comprises detecting signals indicative of said sequences.

15. The method of claim 14, wherein said signals are optical signals.

16. The method of claim 1, wherein said first plurality of nucleic acid molecules comprises a plurality of transcripts.

17. The method of claim 16, further comprising, prior to (d), subjecting said plurality of transcripts to reverse transcription to yield complementary deoxyribonucleic acid (cDNA) molecules, wherein said sequences identified in (d) are sequences of said cDNA molecules.

18. The method of claim 1, wherein said biological sample is a tissue from a subject.

19. The method of claim 1, wherein said second plurality of nucleic acid molecules comprises a functional moiety that couples said second plurality of nucleic acid molecules to said three-dimensional polymer matrix.

20. The method of claim 19, wherein said functional moiety covalently couples said second plurality of nucleic acid molecule to said three-dimensional polymer matrix.

21. The method of claim 1, further comprising contacting said biological sample with a preservation agent.

22. The method of claim 1, wherein said three-dimensional polymer matrix is optically transparent, and wherein (d) comprises optically imaging said three-dimensional polymer matrix to identify said sequences of said second plurality of nucleic acid molecules.

23. The method of claim 1, wherein said first plurality of nucleic acid molecules is covalently bound to said three-dimensional polymer matrix.

24. The method of claim 23, wherein said first plurality of nucleic acid molecules is covalently bound to said three-dimensional polymer matrix via cross-linking.

25. The method of claim 1, wherein said identifying said sequences of said second plurality of nucleic acid molecule comprises hybridizing probes to said second plurality of nucleic acid molecules or derivatives thereof, wherein said probes comprise detectable labels corresponding to said sequences.

26. The method of claim 1, wherein said biological sample is a cell.

* * * * *

UNITED STATES PATENT AND TRADEMARK OFFICE
CERTIFICATE OF CORRECTION

PATENT NO. : 10,494,662 B2
APPLICATION NO. : 15/786921
DATED : December 3, 2019
INVENTOR(S) : Church et al.

Page 1 of 1

It is certified that error appears in the above-identified patent and that said Letters Patent is hereby corrected as shown below:

In the Specification

Under STATEMENT OF GOVERNMENT INTERESTS
Column 1, Line 19:
Please delete "This invention was made with Government support under grant number RC2HL102815 awarded by NHLBI and 1P50HG005550 awarded by NHGRI. The Government has certain rights in the invention." and insert --This invention was made with government support under HG005550 and HL102815 awarded by National Institutes of Health (NIH). The government has certain rights in this invention.--

Signed and Sealed this
Twenty-seventh Day of September, 2022

Katherine Kelly Vidal
*Director of the United States Patent and Trademark Office*